United States Patent [19]

Ketkar et al.

[11] Patent Number: 5,360,467
[45] Date of Patent: Nov. 1, 1994

[54] METHOD OF SEPARATING AND DETECTING IMPURITIES USING A FRACTIONAL CONCENTRATION DETECTOR

[75] Inventors: Suhas N. Ketkar, Allentown; Robert G. Ridgeway, Quakertown; Peter J. Maroulis, Mertztown; Timothy C. Golden, Allentown, all of Pa.

[73] Assignee: Air Products and Chemicals, Inc., Allentown, Pa.

[21] Appl. No.: 101,604

[22] Filed: Aug. 3, 1993

[51] Int. Cl.$^5$ .................. B01D 53/04; B01D 53/22
[52] U.S. Cl. .................... 95/25; 95/56; 95/115; 95/138; 95/148
[58] Field of Search ................ 95/54–56, 95/115, 116, 25, 138, 148

[56] References Cited

U.S. PATENT DOCUMENTS

| | | | |
|---|---|---|---|
| 3,258,896 | 7/1966 | Müller | 95/56 X |
| 3,359,706 | 12/1967 | Zankey | 95/115 X |
| 3,430,417 | 3/1969 | Cree | 95/55 X |
| 3,550,355 | 12/1970 | Remus et al. | 95/54 |
| 3,589,171 | 6/1971 | Haley | 95/56 X |
| 3,638,396 | 2/1972 | Lovelock | 95/56 |
| 3,638,397 | 2/1972 | Charlton | 95/56 |
| 3,690,835 | 9/1972 | Lovelock | 95/56 X |
| 4,238,204 | 12/1980 | Perry | 95/116 X |
| 4,369,048 | 1/1983 | Pence | 95/116 |
| 4,472,176 | 9/1984 | Rubin | 95/56 |
| 4,748,143 | 5/1988 | Tabata et al. | 502/304 |
| 4,957,718 | 9/1990 | Yoo et al. | 423/244 |
| 5,071,626 | 12/1991 | Tuller | 422/98 |
| 5,141,725 | 8/1992 | Ramprasan et al. | 423/249 |

OTHER PUBLICATIONS

*Kirk–Othmer Enc. of Chem. Tech.;* 3rd ed.; 1978 vol. 2; pp. 600–652.

Primary Examiner—Robert Spitzer
Attorney, Agent, or Firm—Geoffrey L. Chase; James C. Simmons; William F. Marsh

[57] ABSTRACT

A method for detection of impurities at very low levels in hydrogen, oxygen or specialty gases comprises the metered mixture with high purity helium and subsequent selective separation of hydrogen, oxygen or specialty gas with the detection of impurities remaining in the helium by ionization spectrometry.

16 Claims, 2 Drawing Sheets

METHOD OF SEPARATING AND DETECTING IMPURITIES USING A FRACTIONAL CONCENTRATION DETECTOR

FIELD OF THE INVENTION

The present invention is directed to separating impurities from a gas stream by commingling the gas stream with a helium gas stream and subsequently separating the impurities with the helium stream while removing the initial gas stream from the impurity-laden helium. More specifically, the present invention is directed to a separation with downstream analysis of the impurity concentration and content. Preferably, bulk hydrogen or oxygen containing impurities can be blended with controlled quantities of pure helium before separation of the helium and impurities from the hydrogen or oxygen and subsequent detection of concentration and/or content of impurities in an atmospheric pressurization mass spectrometer.

BACKGROUND OF THE PRIOR ART

Consumers of industrial gases demand higher and higher purities of such gases wherein impurity contents must be determined, quantified, qualified and monitored down to exceedingly low levels of such impurities typically in the parts per million, parts per billion and in some instances, parts per trillion. Industrial gases being utilized by sensitive manufacturing operations such as semi conductor fabrication facilities, require exceedingly low levels of impurities in gases used in semiconductor fabrication processes, such gases such as hydrogen and oxygen. Various analytical techniques are presently utilized to determine impurity levels in industrial gases such as those supplied to semiconductor fabrication facilities. One such detection device utilized for sensitivity to impurities, particularly at low levels, is an atmospheric pressure ionization mass spectrometer ("APIMS"). Mass spectrometers are known analytical detection devices such as is described in Kirk-Othmer, Encyclopedia of Chemical Technology, 3rd Edition, (1978), Vol. 2, page 600 to 650.

The prior art has broadly described various techniques for separating mixtures of gases, such as hydrogen or oxygen from helium. One such agent useful for selective absorption of oxygen from other gases is the family of inorganic compositions called perovskite. Perovskites possess a cubic crystal structure comprised of $ABO_3$, such as mineral perovskite, $CaTiO_3$. These perovskites are identified in U.S. Pat. No. 4,957,718. Analogous perovskite materials and applications are identified i n U.S. Pat. Nos. 4,748,143 and 5,071,626.

Other material s useful for selective oxygen adsorption from mixed gas streams include cyanocobaltate complexes as identified in U.S. Pat. No. 5,141,725.

It is also known to remove carrier gases such as hydrogen in the feed to a mass spectrometer by diffusion through palladium. See Kirk-Othmer, Encyclopedia of Chemical Technology, 3rd Edition, (1978), Vol. 2, page 644.

Some industrial gases, such as nitrogen, helium and argon, can be analyzed for low level impurity detection directly by injection of a sample of such gas into an APIMS. Hydrogen has been evaluated for impurity content in direct injection into a mass spectrometer, but certain impurities are not readily distinguishable in hydrogen using the best mass spectrometer capabilities. Presently, oxygen cannot be evaluated for potential impurities by direct injection in an APIMS. Therefore, a need exists for a method for detecting and analyzing impurities of a broad spectrum in hydrogen and a comparable need to analyze oxygen for any impurity is also sought.

The present invention overcomes the difficulties in analyzing and detecting low concentration levels of impurities in industrial gases destined for high purity end uses by effectively transferring the impurities to a high ionization potential gas and selectively removing the gas being sampled before detection in an appropriate detector for concentration and quantification of such impurities, as will be set forth in greater detail below.

BRIEF SUMMARY OF THE INVENTION

The present invention is a method for detecting impurities in a gas stream in a fractional concentration detector comprising the steps of:
a) mixing the gas stream with a high purity carrier gas stream in an appropriate ratio to produce a gas mixture;
b) contacting the gas mixture with a separatory medium selective for separating the gas stream over the impurities and the carrier gas;
c) separating the gas stream from any impurities and the carrier gas to produce a carrier gas stream containing essentially all of any impurities;
d) introducing the carrier gas stream containing essentially all of the impurities into a fractional concentration detector to detect the impurities in the carrier gas stream; and
e) detecting the concentration and/or type of impurities in the carrier gas stream.

Preferably the gas stream is hydrogen and the separatory medium is a palladium-containing diffuser which allows the hydrogen to pass through it as a permeate and resulting in the carrier gas stream containing essentially all of the impurities as a reject stream.

Alternatively, the gas stream is oxygen and the separatory medium is an oxygen selective adsorbent which preferentially absorbs oxygen and results in the carrier gas stream containing essentially all of the impurities as an unadsorbed effluent.

Preferably the adsorbent is selected from the group consisting of perovskites, cyanocobaltate complexes and mixtures thereof.

Preferably the oxygen is adsorbed on the adsorbent, the carrier gas stream and any impurities pass through the adsorbent essentially unadsorbed to form the carrier gas stream containing essentially all of the impurities, contact of the gas mixture on the adsorbent is terminated, the adsorbent is heated, and adsorbed oxygen is desorbed to regenerate the adsorbent.

Preferably there are at least two beds of adsorbent and while one bed is contacted with the gas mixture, another bed is heated to desorb oxygen and regenerate its adsorbent.

Preferably the concentration of impurities in the gas stream is below approximately 1 part per million, more preferably 100 parts per billion, most preferably 100 parts per trillion. Preferably the fractional concentration detector is an atmospheric pressure ionization mass spectrometer.

Preferably, a flowrate of the carrier gas stream is used, which is less than the flowrate of the gas stream containing the impurities, to concentrate the impurities in the carrier gas stream when the gas stream is separated from the carrier gas stream containing essentially all of any impurities for enhanced detection of the impurities.

Preferably, the carrier gas is selected from the group consisting of helium, argon, nitrogen or mixtures thereof. More preferably the carrier gas is helium.

In a specific example, the present invention is a method for detecting impurities in a hydrogen gas stream in a fractional concentration detector comprising the steps of:
a) mixing the hydrogen gas stream with a high purity helium stream in an appropriate ratio to produce a gas mixture;
b) contacting the gas mixture with a palladium containing diffuser which allows the hydrogen to pass through it as a permeate stream while producing a helium stream containing essentially all of the impurities as a reject stream;
c) separating the hydrogen gas stream from any impurities and from the helium to produce a helium stream containing essentially all of any of the impurities;
d) introducing the helium stream containing essentially all of the impurities into the fractional concentration detector to detect the impurities in the helium stream; and
e) detecting the concentration and/or type of impurities in the helium stream.

In another specific example the present invention is a method for detecting impurities in an oxygen gas stream in a fractional concentration detector comprising the steps of:
a) mixing the oxygen gas stream with a high purity helium stream in an appropriate ratio to produce a gas mixture;
b) contacting the gas mixture with an oxygen selective adsorbent which preferentially adsorbs oxygen while producing a helium stream containing essentially all of the impurities as an unadsorbed effluent;
c) separating the oxygen gas stream from any impurities and from the helium to produce a helium stream containing essentially all of any of the impurities;
d) introducing the helium stream containing essentially all of the impurities into the fractional concentration detector to detect the impurities in the helium stream; and
e) detecting the concentration and/or type of impurities in the helium stream.

Another specific example of the present invention is a method for detecting impurities in a specialty gas stream in a fractional concentration detector comprising the steps of:
a) mixing the specialty gas stream with a high purity helium stream in an appropriate ratio to produce a gas mixture;
b) contacting the gas mixture with a column packed with a material which has a longer retention time for the specialty gas than while the helium stream containing essentially all of the impurities as an effluent having a shorter retention time on the column;
c) separating the specialty gas stream from any impurities and from the helium to produce a helium stream containing essentially all of any impurities;
d) introducing the helium stream containing essentially all of the impurities into the fractional concentration detector to detect the impurities in the helium stream; and
e) detecting the concentration and/or type of impurities in the helium stream.

DETAILED DESCRIPTION OF THE INVENTION

Figure 1:
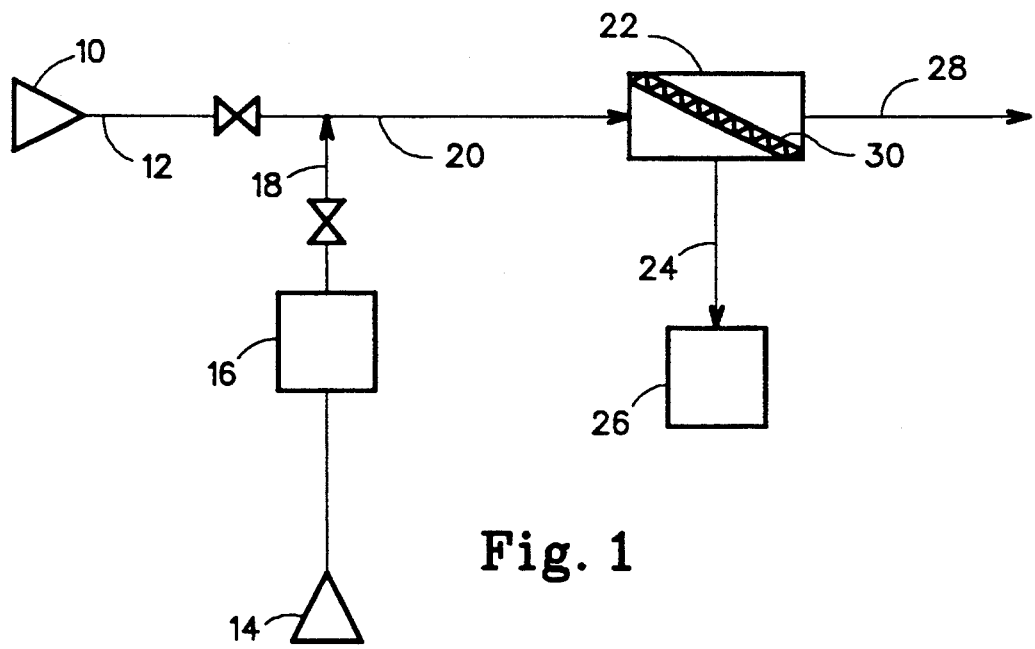
FIG. 1 is a schematic illustration of a first preferred embodiment of the present invention.

The present invention is a unique process for analyzing industrial gases for impurity concentration and characterization of those impurities. A wide array of industrial gases are amenable to analysis with the present invention, such as argon, nitrogen, methane, carbon monoxide, carbon dioxide, noble or rare gases and specialty gases such as hydrogen chloride or tungsten hexafluoride, but hydrogen, oxygen and specialty gases are particularly appropriate gases which may be analyzed for impurities by the present invention.

The impurities which may be detected and analyzed for impurity concentration and impurity character encompass a wide range of impurities including moisture, other undesired industrial gases as listed above in a desired industrial gas, hydrocarbons and volatile metals which may become entrained in gases during transit through metallic conduits.

As stated above, the present invention allows an industrial gas, such as hydrogen, oxygen or specialty gases, to be sampled by taking a slip stream from a bulk gas stream going to a sensitive end use, such as a semiconductor fabrication facility, and allows blending of the gas stream with a highly purified carrier gas that has a higher ionization potential than any of the impurities expected in the industrial gas, such as argon, nitrogen or helium, which is best suited to this duty because of its highest ionization potential of any element. Therefore, the carrier gas preferably is a helium gas stream wherein high purity is at least 99.99999% helium in a controlled and calibrated ratio such that the concentration of impurities in the initial industrial gas stream can be determined after detecting the concentration of impurities in a subsequently isolated helium gas stream. This can be accomplished by appropriate precision metering of the gas stream containing the impurities and the high purity helium stream when mixing the two streams in a common conduit.

The initial gas stream, such as hydrogen, oxygen or specialty gases, is then selectively removed or separated in the separatory medium, such as a semipermeable membrane, an absorption bed of adsorbent selective for the initial gas stream and non-selective for the helium gas stream and the various impurities or a packed column having a long retention time for the initial gas stream and a short retention time for the helium gas stream and the various impurities. In this manner, the impurities are effectively conveyed from the initial gas stream of hydrogen or oxygen to the introduced and metered helium gas stream, while the two gas components of the resulting gas mixture are separated. The resulting hydrogen or oxygen of the initial gas stream may be vented, while the helium gas stream containing essentially all of the impurities is subjected to analysis for impurity concentration and type or character of impurities by injection into an appropriate fractional concentration detector.

In the context of the present invention, a fractional concentration detector is any appropriate impurity sensitive detection analytical instrumentation which is capable of determining concentrations of impurities from the helium gas stream at the low levels of impurity concentration identified for the present invention, specifically at or below 1 part per million, preferably 100 parts per billion and more preferably 100 parts per trillion. Such analytical detection devices include various forms of spectrometers or gas chromatographs, but most preferably the fractional concentration detector is an atmospheric pressure ionization mass spectrometer ("APIMS"). Mass spectrometers come in a wide variety of types, but generally mass spectrometry utilizes the travel of ionized components of the material to be analyzed along well defined trajectories in an evacuated system. Typically, a reservoir for receiving the sample to be analyzed communicates with an ionization chamber which may be provided with an ionization source, such as an electron beam where the sample is ionized and passes out of the ionization chamber by electrostatic forces and assisted by carrier gases in some events which are removed by evacuation mechanisms. Ions pass through electrostatic analyzer portions and potentially magnetic analyzer portions before being focused through an appropriate slit and detected by a sensitized collector which then provides an electrical signal amplified and recorded by appropriate means well known in the art. Quantitative and qualitative determination of impurities in a gas stream initially containing such impurities is capable through such spectrometers.

In an APIMS, ionization takes place at pressures of 1 atmosphere or above. Usually, the ionization in a mass spectrometer takes place in vacuum (typically at pressures below 0.001 torr). Typically, electrons from a hot filament are used to ionize the sample gas present in this low pressure ionization region. The electrons ionize a fraction of the molecules present in this region. The ions that are formed travel through a set of lenses into the mass spectrometer where they are sorted according to their mass and recorded. Since the mass spectrometer is housed in vacuum, the ions do not collide with any other molecules while they are traversing the mass spectrometer. The number of ions of any impurity that are formed in the ionization region depend upon the number of molecules of that impurity that are present in the ionization region and the cross section for ionization of that particular impurity. The ionization cross section is a natural constant and is usually very low for any impurity. Typically, mass spectrometers that use electrons to ionize can measure impurities in the few parts per million concentration range. In a few favorable cases, one can measure concentrations below 1 part per million.

The parameter limiting the ability to detect lower concentrations is the ionization cross section. In APIMS, this limitation is avoided by using an indirect scheme of ionization. In APIMS, the ionization is performed at high pressure (1 atmosphere or more). At this high pressure, the total number of gas molecules present in the ionization region are much more than what would be present if the pressure was lower (as is the case with conventional mass spectrometer). Electrons, produced from a corona discharge, are used to ionize the gas molecules present in the ionization region. These electrons will ionize a fraction of the bulk gas and impurity molecules, the fraction depending upon the relevant ionization cross sections. Even though the ionization cross section is low, there are a large number of molecules present in the ionization region, and it will produce a substantial amount of bulk gas ions. In addition, a small number of impurity molecules will also be ionized. If one considers the case of a gas "B" with impurity "T," there will be a large number of ions of "B" and a small amount of ions of "T." As these ions move towards the mass spectrometer, they will collide with the molecules present in the ionization region. At a pressure of 1 atmosphere, on average, an ion will collide with another ion or molecule over one hundred thousand times while traversing a distance of 1 mm. Every time the ion of "B" collides with the impurity molecule "T," if the ionization potential of "B" is greater than that of "T," there is a chance that it will ionize "T." The cross section for this kind of ion-molecule reaction is more favorable than the cross section for electron impact ionization. As the ions of "B" collide with "T," they will ionize "T," thereby producing a large number of ions of "T" at the exit of the ionization chamber. These ions are then drawn into a vacuum chamber and analyzed by a mass spectrometer.

The ionization of "T" occurs only if the ionization potential of "T" is less than that of "B," a limitation exists on the impurities that can be measured using APIMS. Helium has the highest ionization potential and, consequently, APIMS can be used to measure any impurity in helium. On the other hand, oxygen has one of the lowest ionization potentials, and thus APIMS cannot be used to measure any impurities in oxygen.

Every time an impurity molecule is ionized, an ion of "B" looses its charge and becomes an uncharged molecule. This places a restriction on the maximum concentration of impurity that can be measured by an APIMS. Typically, an APIMS is used to measure impurity concentration below 100 parts per billion. It has enough sensitivity to measure some impurities in the part per quadrillion concentration range.

The separatory medium can be selected from copper-based deoxo units to remove oxygen, hydrogen storage alloys to remove hydrogen, porous polymers to remove tungsten hexafluoride, hydrogen fluoride or calcium fluoride, and generally selective materials which are selective for the gas stream being measured and not selective for the anticipated impurities or the carrier gas (such as helium).

In one form of the present invention wherein a gas stream, such as an impurity containing hydrogen stream, is mixed with high purity helium, the hydrogen is subsequently removed from the helium stream containing essentially all of the impurities by contact of the gas mixture with a palladium diffuser comprising a palladium-containing porous surface which is selectively permeable to hydrogen creating a hydrogen permeate stream essentially separated from helium and the contained impurities, while producing a helium stream containing essentially all of the impurities as a reject stream on the initial side of the palladium diffuser. The palladium diffuser is a well known material having appropriate hydrogen selectivity as set forth in Kirk-Othmer, Encyclopedia of Chemical Technology, 3rd Edition, Vol. 2 (1978), page 644.

Alternatively, in contrast to the use of a palladium diffuser membrane surface, it is possible to separate an oxygen gas stream to be analyzed, such as oxygen containing impurities, by comparable mixture with a high purity helium stream and subsequent separation of the oxygen using a separatory medium of parallel beds of an oxygen selective adsorbent, wherein the oxygen is selectively adsorbed on the adsorbent, while the helium and essentially all of the impurities originally contained in the oxygen gas stream pass through the adsorbent bed for subsequent analysis. Appropriate adsorbents which are selective for oxygen under these circumstances include cyanocobaltate complex exemplified by materials represented by the chemical formula $A_{x/z}{}^{z+}\cdot[CO(CN)_n]^{x-}\cdot pS$ where A is an alkali, alkaline earth, transition or Group XII metal atom; z is 1, 2 or 3; n is any number from 3 to 5; x is n-2; p is any number from greater than zero to 6 and S is a ligand which is capable of coordinating with $A^{z+}$, Co or both. Such materials are described in U.S. Pat. No.5,141,725, the text of which is incorporated by reference herein in its entirety. Appropriate oxygen selective adsorbents also include perovskite which generally has the crystalline structure defined by the empirical formula $ABO_3$ in which A and B are cations of two different metals in which the A cation is coordinate to 12 oxygen atoms while the B cation occupies octahedral sites and is coordinated into 6 oxygen atoms. For example, compound $LaMnO_3$ is an appropriate perovskite structure. Also appropriate is the mineral perovskite having a cubic crystal structure comprising $CaTiO_3$. Such appropriate perovskites are described in U.S. Pat. Nos. 4,957,718; 4,748,143 and 5,071,626, the specifications of which are incorporated herein in their entirety.

The present invention will now be described in greater detail with respect to several preferred embodiments of the invention. With regard to FIG. 1, a first embodiment of the present invention will be described for a hydrogen gas stream containing impurities which is selectively separated with the separatory media of a palladium diffuser. A hydrogen gas stream containing impurities, such as argon, nitrogen and/or methane, has a slip stream 10 removed from the bulk flow of the hydrogen stream and passed through conduit 12 controllably flowing through an appropriate valve.

This hydrogen gas stream is mixed with a high purity source of helium carrier gas wherein the helium source 14 passes through an appropriate purifier 16 comprising a getter material, such as a zirconium alloy, and passing through conduit 18 flowing controllably through appropriate valving. By operation of the valving, in appropriately dimensioned conduits, the exact relationship or ratio of flows of the hydrogen in conduit 12 and the high purity helium in conduit 18 can be determined so that ultimately the concentration of impurities and their character in the initial hydrogen gas stream can be ascertained.

The resulting gas mixture of impurity-containing hydrogen and helium is passed as a gas mixture through conduit 20 and is introduced into a separatory medium 22 comprising an appropriate vessel having a palladium diffuser membrane surface 30. The hydrogen selectively passes through the palladium diffuser surface 30 as a permeate being removed for vent in conduit 28.

The helium gas stream containing essentially all of any existing impurities are rejected by the palladium diffuser membrane surface 30 and are removed from the separatory medium 22 in conduit 24. The impurity concentration and character of the helium gas stream in conduit 24 is then introduced into a fractional concentration detector 26, such as an atmospheric pressure ionization mass spectrometer.

By blending the impurity bearing hydrogen gas stream with a high purity helium gas stream and subjecting the gas mixture to hydrogen selective separation, the impurities in the hydrogen gas stream are effectively shifted to the helium gas stream wherein helium has the highest ionization potential of any element. Therefore, in the operation of an ionization spectrometer detection device, the impurities will most readily be determined in the helium carrier gas in contrast to the original industrial gas or gas stream in which the impurities existed. This provides for a very sensitive detection of impurities at very low concentration levels, including down to 1 part per trillion or less of impurities in the original gas stream.

By determining the impurity concentration and character from the helium gas stream in the atmospheric pressure ionization mass spectrometer and utilizing the metered, controlled mixture of the hydrogen gas stream with the helium gas stream, the concentration of the hydrogen gas stream can be readily ascertained from the concentration of impurities detected in the helium gas stream. This is achieved by the relationship of $C(i)$ which is the fractional concentration of an impurity "i" in a hydrogen gas stream. The fractional concentration of the impurity "i" in helium will be $C(i)$ multiplied by the ratio $F2/F1$ where $F2$ is the hydrogen flow rate and $F1$ is the helium flow rate at the point of mixture of the two gas streams.

The first embodiment described above is appropriate for impurity detection in hydrogen gas streams which are selective to permeation through the palladium diffuser. However, another industrial gas which is readily used in semiconductor fabrication facilities where ultra-high purities are demanded is oxygen. Oxygen is inappropriate for selective separation through palladium diffusers. However, oxygen is readily selectively adsorbed very completely by several high performance adsorbents, such as perovskites and cyanocobaltate complexes. This means that oxygen can be analyzed in a similar context as with regard to the first embodiment, but using switching temperature swing adsorption in parallel adsorption beds for the separatory medium as described below for the second embodiment.

Figure 2:
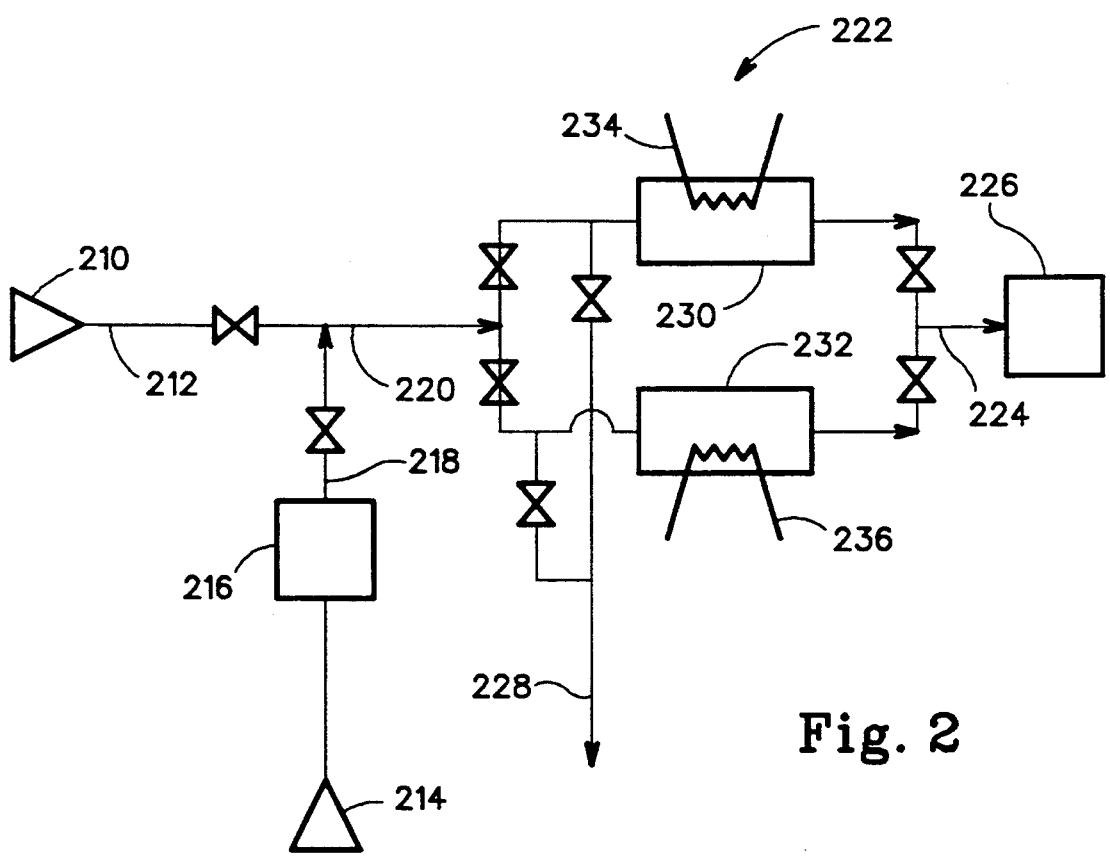
FIG. 2 is a schematic illustration of a second preferred embodiment of the present invention.

With reference to FIG. 2, a bulk gas stream of oxygen has a slip stream removed 210 to pass through conduit 212 controllably by appropriate valving. A high purity source of helium is produced by providing a source of helium 214 which passes through a purifier 216 comprising a getter material, such as a zirconium alloy, and resulting in a high purity helium stream of 99.99999% helium in conduit 218 controllably flowing by appropriate valving. By use of metered valving in precise dimensioned conduits and mixing zones, a gas mixture of oxygen containing impurities and helium results in conduit 220 of known volume and flow of the respective component gas mixtures. The gas mixture in line 220 enters one of two adsorbent beds 230 and 232 comprising a separatory medium 222.

For purposes of this discussion, the gas mixture in conduit 220 enters parallel adsorbent bed 230 and is subjected to selective oxygen adsorption on a perovskite or cyanocobaltate complex with the passage of the helium and essentially all of the impurities through the bed as an effluent emanating through line 224 for detection in a fractional concentration detector 226, such as an atmospheric pressure ionization mass spectrometer.

While adsorption bed 230 is on line, adsorption bed 232 is being heated by heater 236 comprising any appropriate source of heat such as steam, electric resistance or other containing heat sources to result in the desorption at elevated temperature, such as 350° C., of the previously adsorbed oxygen from the gas mixture flowing through line 220.

This oxygen is removed by appropriate valve operation through conduit 228 either at atmospheric pressure or by the assistance of vacuum created by a venturi or vacuum pump, not illustrated. When adsorption bed 230 is saturated with oxygen and adsorption bed 232 has been regenerated by high temperature desorption, appropriate valving is used to change the flow of the gas mixture in line 220 to adsorption bed 232 while adsorption bed 230 is regenerated in a comparable matter by application of the heat through heater 234 and removal of desorbed oxygen through appropriate valving in conduit 228.

In this manner the impurities contained in the oxygen gas stream are effectively transferred to the helium gas stream under known volumetric flow admixture so that the impurity detection conducted on the helium gas stream in conduit 224 or the spectrometer 226 can readily be related back to the impurity concentration of the oxygen gas 210. Again, this extrapolation is conducted by the relationship of C(i) constituting the fractional concentration of an impurity "i" in the oxygen wherein the fractional concentration of the impurity "i" in helium will be C(i) multiplied by the ratio F2/F1 wherein the oxygen flow rate is F2 and the helium flow rate is F1.

Other industrial gases which are readily used in semiconductor fabrication facilities where ultrahigh purities are demanded are specialty gases such as hydrogen chloride or tungsten hexafluoride. Specialty gases are inappropriate for selective separation through palladium diffusers or adsorbents, such as perovskites and cyanocobaltate complexes. This means that specialty gases can be analyzed in a similar context as with regard to the first and second embodiments, but using a porous polymer packed column for the separatory medium as described below for the third embodiment.

Figure 3:
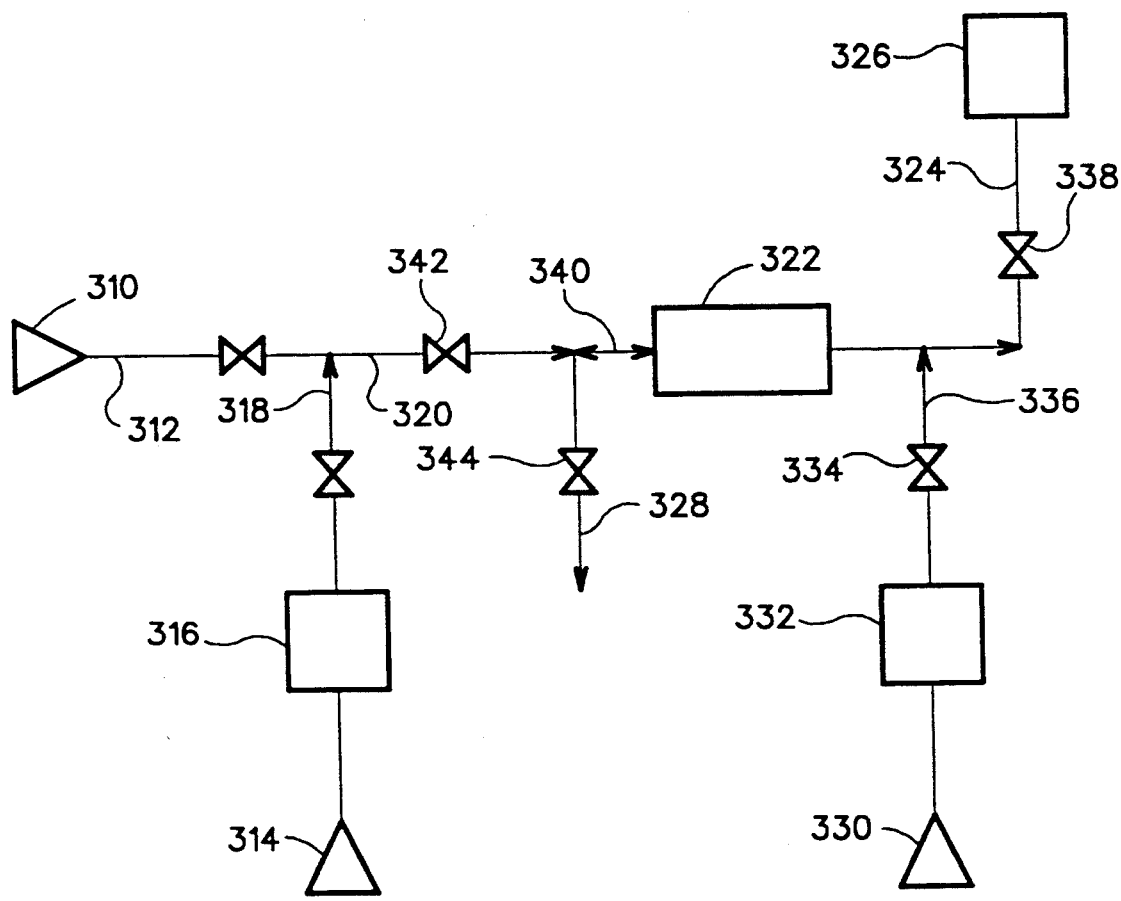
FIG. 3 is a schematic illustration of a third preferred embodiment of the present invention.

With reference to FIG. 3, a bulk gas stream of hydrogen chloride has a slip stream removed 310 to pass through conduit 312 controllably by appropriate valving. A high purity source of helium is produced by providing a source of helium 314 which passes through a purifier 316 comprising a getter material, such as a zirconium alloy, and resulting in a high purity helium stream of 99.99999% helium in conduit 318 controllably flowing by appropriate valving. By use of metered valving in precise dimensioned conduits and mixing zones, a gas mixture of hydrogen chloride containing impurities and helium results in conduit 320 of known volume and flow of the respective component gas mixtures. The gas mixture in line 320 passes through valve 342 and line 340 and enters a porous polymer packed column comprising a separatory medium 322.

For purposes of this discussion, the gas mixture in conduit 320 enters packed column 322 and the hydrogen chloride is subjected to relatively longer elution or retention time on the porous polymer than the helium and essentially all of the impurities, which experience a relatively short elution or retention time on the porous polymer packing and are the first effluent emanating through open valve 338 and line 324 for detection in a fractional concentration detector 326, such as an atmospheric pressure ionization mass spectrometer.

Prior to breakthrough of hydrogen chloride through the packed column 322, valve 334 is opened and a second source 330 of high purity helium is passed through a purifier 332, line 336 and enters the column 322 to rinse the hydrogen chloride out through line 340, open valve 344 and vent line 328 to appropriate vent or scrubbing. Valve 342 is closed during the rinse of the column. Valve 338 may remain open during the rinse to continue to pass the helium carrier gas through the detector 326.

In this manner the impurities contained in the hydrogen chloride gas stream are effectively transferred to the helium gas stream under known volumetric flow admixture so that the impurity detection conducted on the helium gas stream in conduit 324 or the spectrometer 326 can readily be related back to the impurity concentration of the hydrogen chloride gas 310. Again, this extrapolation is conducted by the relationship of C(i) constituting the fractional concentration of an impurity "i" in the hydrogen chloride wherein the fractional concentration of the impurity "i" in helium will be C(i) multiplied by the ratio F2/F1 wherein the hydrogen chloride flow rate is F2 and the helium flow rate is F1.

Detection capability of the present invention can be enhanced by judicious selection of the relative flowrates of the gas stream bearing tile impurities and the carrier gas stream. By using a carrier gas flowrate less than the gas stream flowrate, the concentration of the impurities for detection can be increased after separation of the gas stream from the carrier gas stream by an amount corresponding to the relative flowrates. For instance, if a helium carrier gas flowrate is ten times less than the flowrate of the gas stream containing impurities, then the detector will experience a ten time fractional concentration increase of impurities. An impurity initially at 1 ppb concentration in the gas stream will become 10 ppb in the helium stream going to the detector. The limits of the flowrate differential are only set by the capacity and relative selectivity of the separatory device such as a membrane or adsorbent for a gas stream, such as hydrogen or oxygen over helium.

The present invention allows for the analysis of extremely low levels of impurities in otherwise difficult gas streams to be analyzed, such as hydrogen and oxygen. With regard to hydrogen, past attempts to analyze hydrogen for impurities resulted in some problematic impurities, such as argon, being difficult if not impossible to detect, particularly at ultra-low levels. The present invention allows a wide spectrum of such impurities to be detected in a hydrogen gas stream by effectively replacing the hydrogen with helium which is readily separated from and distinguished from impurities in an ionization spectrometer. Likewise, oxygen which has previously been incapable of detection analysis for impurities, particularly at the ultra-low levels of impurities described with regard to the present invention and semiconductor fabrication demands, is easily subject to low level impurity detection in the present invention where again helium is controllably and quantifiably used to carry the impurities originally carried by the oxygen making subsequent detection quantitatively and qualitatively of impurities in the helium easily in an ionization spectrometer wherein otherwise oxygen could not have been subject to such low level impurity detection at all. These significant resolutions of the existing problems of low level impurity detection in problematic gas streams, such as hydrogen or oxygen, overcome the existing shortcomings of the prior art modes of impurity detection and provide a surprising enhancement in the ability to calibrate purity level s in such gas streams.

The present invention has been described with regard to several preferred embodiments however, the full scope of the invention should be ascertained from the claims which follow.

We claim:

1. A method for detecting impurities in a bulk gas stream in a fractional concentration detector comprising the steps of:
   a) taking a slip stream from said bulk gas stream to be subject to detection of contained impurities;
   b) mixing said slip stream with a high purity carrier gas stream in an appropriate ratio to produce a gas mixture wherein said carrier gas has a higher ionization potential than any of said impurities;
   c) contacting said gas mixture with a separatory medium selective for separating said slip stream from said impurities and said carrier gas;
   d) separating said slip stream from any impurities and from said carrier gas by said separatory medium to produce a carrier gas stream containing essentially all of any said impurities;
   e) introducing said carrier gas stream containing essentially all of said impurities into said fractional concentration detector to detect the impurities in said carrier gas stream; and
   f) detecting the concentration and/or type of impurities in said carrier gas stream.

2. The method of claim 1 wherein said slip stream is hydrogen and said separatory medium is a palladium containing diffuser which allows said hydrogen to pass through it as a permeate stream while producing said carrier gas stream containing essentially all of said impurities as a reject stream.

3. The method of claim 1 wherein said slip stream is oxygen and said separatory medium is an oxygen selective adsorbent which preferentially adsorbs oxygen while producing said carrier gas stream containing essentially all of said impurities as an unadsorbed effluent.

4. The method of claim 3 wherein said adsorbent is selected from the group consisting of perovskites, cyanocobaltate complexes and mixtures thereof.

5. The method of claim 3 wherein said oxygen is adsorbed on said adsorbent, said carrier gas stream and any said impurities pass through said adsorbent essentially unadsorbed to form said carrier gas stream containing essentially all of said impurities, contact of said gas mixture on said adsorbent is terminated, said adsorbent is heated, and adsorbed oxygen is desorbed to regenerate the adsorbent.

6. The method of claim 5 wherein there are at least two beds of adsorbent and while one bed is contacted with said gas mixture another bed is heated to desorb oxygen and regenerate its adsorbent.

7. The method of claim 1 wherein the concentration of said impurities in said bulk gas stream is below approximately 1 part per million.

8. The method of claim 7 wherein the concentration of said impurities in said bulk gas stream is below approximately 1 part per billion.

9. The method of claim 7 wherein the concentration of said impurities in said bulk gas stream is below approximately 1 part per trillion.

10. The method of claim 1 wherein said fractional concentration detector is an atmospheric pressure ionization mass spectrometer.

11. The method of claim 1 wherein a flowrate of said carrier gas stream is used which is less than a flowrate of said slip stream containing said impurities to concentrate said impurities in said carrier gas stream when said slip stream is separated from said carrier gas stream containing essentially all of any said impurities for enhanced detection of said impurities.

12. The method of claim 1 wherein said carrier gas is selected from the group consisting of helium, nitrogen, argon or mixtures thereof.

13. The method of claim 1 wherein said carrier gas is helium.

14. A method for detecting impurities in a bulk hydrogen gas stream in a fractional concentration detector comprising the steps of:
   a) taking a slip stream from said bulk hydrogen gas stream to be subject to detection of contained impurities;
   b) mixing said slip stream with a high purity helium stream in an appropriate ratio to produce a gas mixture wherein said helium stream has a higher ionization potential than any of said impurities;
   c) contacting said gas mixture with a palladium containing diffuser which allows hydrogen of said gas mixture to pass through it as a permeate stream while producing a helium stream containing essentially all of said impurities as a reject stream;
   d) separating said hydrogen from any impurities and from said helium by said separatory medium to produce a helium stream containing essentially all of any said impurities;
   e) introducing said helium stream containing essentially all of said impurities into said fractional concentration detector to detect the impurities in said helium stream; and
   f) detecting the concentration and/or type of impurities in said helium stream.

15. A method for detecting impurities in a bulk oxygen gas stream in a fractional concentration detector comprising the steps of:
   a) taking a slip stream from said bulk oxygen gas stream to be subject to detection of contained impurities;
   b) mixing said slip stream with a high purity helium stream in an appropriate ratio to produce a gas mixture wherein said helium stream has a higher ionization potential than any of said impurities;
   c) contacting said gas mixture with an oxygen selective adsorbent which preferentially adsorbs oxygen of said gas mixture while producing a helium stream containing essentially all of said impurities as an unadsorbed effluent;
   d) separating said oxygen from any impurities and from said helium to produce a helium stream containing essentially all of any said impurities;
   e) introducing said helium stream containing essentially all of said impurities into said fractional concentration detector to detect the impurities in said helium stream; and
   f) detecting the concentration and/or type of impurities in said helium stream.

16. A method for detecting impurities in a bulk specialty gas stream in a fractional concentration detector comprising the steps of:

a) taking a slip stream from said bulk specialty gas stream to be subject to detection of contained impurities;
b) mixing said slip stream with a high purity helium stream in an appropriate ratio to produce a gas mixture wherein said helium stream has a higher ionization potential than any of said impurities;
c) contacting said gas mixture with a column packed with a material which has a longer retention time for said specialty gas in said slip stream than said helium stream containing essentially all of said impurities as an effluent having a shorter retention time on said column;
d) separating said slip stream from any impurities and from said helium on said column to produce a helium stream containing essentially all of any said impurities;
e) introducing said helium stream containing essentially all of said impurities into said fractional concentration detector to detect the impurities in said helium stream; and
f) detecting the concentration and/or type of impurities in said helium stream.

* * * * *